United States Patent [19]

Crossley

[11] 4,349,480
[45] Sep. 14, 1982

[54] PROCESS FOR PREPARING 1-(3-BROMO-2-ALKYLPROPANOYL-L-PROLINE DERIVATIVES

[75] Inventor: Roger Crossley, Reading, England

[73] Assignee: John Wyeth & Brother Limited, Maidenhead, England

[21] Appl. No.: 236,350

[22] Filed: Feb. 20, 1981

[30] Foreign Application Priority Data

Feb. 26, 1980 [GB] United Kingdom ............... 8006414

[51] Int. Cl.³ .................. C07D 207/16; C07D 209/18
[52] U.S. Cl. ...................... 260/326.2; 260/326.11 R; 260/239.3 B
[58] Field of Search ..................... 260/326.2, 326.11 R

[56] References Cited

U.S. PATENT DOCUMENTS

| | | | |
|---|---|---|---|
| 4,105,776 | 8/1978 | Ondetti et al. | 424/274 |
| 4,127,535 | 11/1978 | Coy et al. | 260/112.5 R |
| 4,129,566 | 12/1978 | Ondetti et al. | 260/326.2 |
| 4,154,935 | 5/1979 | Ondetti et al. | 260/326.2 |
| 4,192,945 | 3/1980 | Ondetti | 546/245 |
| 4,291,040 | 9/1981 | Krapcho | 260/326.2 |

OTHER PUBLICATIONS

Buehler et al., Survey of Organic Synthesis, John Wiley & Sons Inc., 1970, p. 896.
March, Advanced Org. Chem. Reactions, Mechanisms and Structure, p. 81.

*Primary Examiner*—Jane T. Fan
*Attorney, Agent, or Firm*—Richard K. Jackson

[57] ABSTRACT

The invention relates to the preparation of 1-bromo-2-D-alkylpropanoyl-L-proline derivatives and analogous compounds which are useful as chemical intermediates to angiotensin converting enzyme (ACE) inhibitors and to the stereospecific synthesis of such ACE inhibitors having the formula:

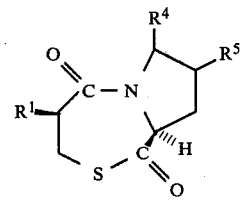

wherein $R^1$ is lower alkyl and $R^4$ and $R^5$ are both hydrogen or together with the carbons to which they are attached represent a benzene ring optionally substituted by defined substituents. Intermediates of formula

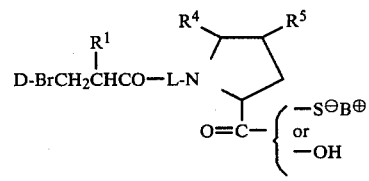

are also disclosed wherein $R^1$, $R^4$, $R^5$ are as defined above and $B^+$ is a cation.

4 Claims, No Drawings

PROCESS FOR PREPARING 1-(3-BROMO-2-ALKYLPROPANOYL-L-PROLINE DERIVATIVES

This invention relates to novel processes for preparing L-proline derivatives useful as chemical intermediates and to the preparation of pharmaceutically active L-proline derivatives.

U.S. Pat. No. 4,105,776 published Aug. 8, 1978 discloses proline derivatives which are stated to inhibit the conversion of the decapeptide angiotensin I to angiotensin II and are therefore useful in reducing or relieving angiotensin related hypertension. The proline derivatives are disclosed as having general formula (A)

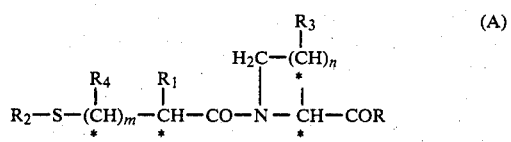

wherein R is hydroxy, $NH_2$ or lower alkoxy; $R_1$ and $R_4$ each is hydrogen, lower alkyl, phenyl or phenyl-lower alkyl; $R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

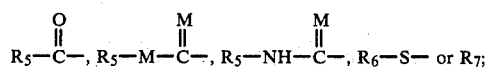

$R_3$ is hydrogen, hydroxy or lower alkyl; $R_5$ is lower alkyl, phenyl or phenyl-lower alkyl; $R_6$ is lower alkyl, phenyl, substituted phenyl, (wherein the phenyl substituent is halo, lower alkyl or lower alkoxy), hydroxy-lower alkyl or amino(carboxy)lower alkyl;

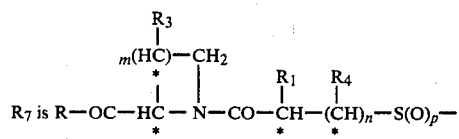

M is O or S; m is 1 to 3; n and p each is 0 to 2 and processes for preparing them. The asterisks indicate asymmetric carbon atoms.

The preferred isomeric form is stated to be the L-isomer with respect to the carbon of the amino acid, and the D-isomer with respect to the carbon bearing $R_1$. For the purposes of the present application such a preferred arrangement of asymmetric centres is termed 'D, L configuration'.

A compound falling within the above mentioned formula and described therein, namely 1-(3-mercapto-2-D-methylpropanoyl)-L-proline having the generic name captopril, has been extensively investigated and found to be a potent antihypertensive agent (see for example, D. W. Cushman et al, *Biochemistry*, Vol. 16, 5484 (1977); D. W. Cushman et al, *Prog. in Cardiovascular Diseases*, Vol. XXI, No. 3, 183 (1978); *Chemistry and Engineering*, April 4, 21 (1977); and H. Gavras et al., *New Eng. J. Med.*, Vol. 298, No. 18, 991 (1978). This compound has the preferred D, L configuration.

U.S. Pat. No. 4,105,776 also describes a route for the preparation of captopril and related compounds using as intermediates compounds of formula (B)

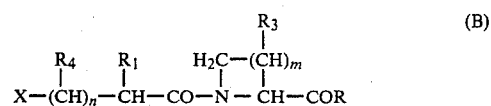

wherein R, $R_1$, $R_3$, $R_4$, m and n are as defined above and X is halogen. Such compounds of formula (B) are prepared by reacting an activated form of an acid of formula (C)

with an acid of formula (D)

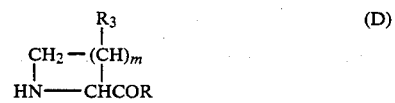

We have now surprisingly found a process for preparing intermediate compounds falling within the scope of formula (B), which employs mixtures of stereoisomers falling within formula (C) and which provides increased proportions of intermediates having the same D, L configuration of asymmetric centres as for captopril. Thus the process of this invention is particularly useful for increasing the proportion of D, L intermediates when a racemic acid within formula (C) is used as precursor, thereby giving increased yields of the desired diastereoisomer.

The process of this invention is also useful for preparing other intermediates within the disclosure of South African Patent Application No. 80/4946 and European Patent Application No. 80302784.6, Publication No. EP24852, having the formula (E)

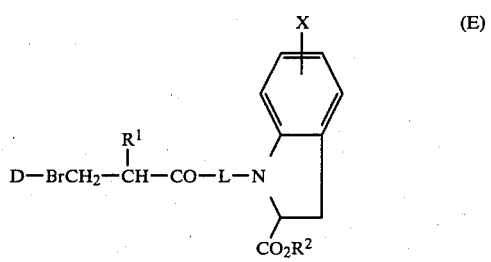

wherein $R^2$ is a carboxy protecting group, X is hydrogen or a substituent selected from hydroxy, lower alkyl, lower alkoxy and halogen, and $R^1$ is alkyl of 1 to 4 carbon atoms. Such compounds (E) fall within a class of intermediates disclosed in South African Patent Application No. 80/4946 as useful for preparing final products useful for treating angiotensin related hypertension. Some of these final products may be represented by the general formula

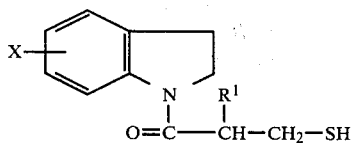

(F)

where X and R¹ are as defined above.

Accordingly this invention provides a process for preparing a compound of formula (I)

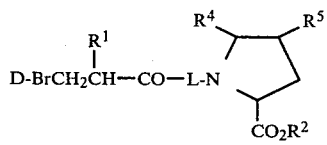

(I)

in excess of the corresponding L, L diastereoisomer wherein R¹ is lower alkyl, R² is a carboxy protecting group, R⁴ and R⁵ are either both hydrogen or together with the carbon atoms to which they are attached represent a fused benzene ring optionally substituted by hydroxy, lower alkyl, lower alkoxy and halogen, which comprises reacting an enantiomeric mixture of an acid of formula (II)

(II)

with a carbodiimide or carbonyl diimidazole coupling agent and a compound of formula (III)

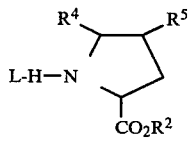

(III)

in which formulae R¹, R², R⁴ and R⁵ are as defined above.

By the term 'lower alkyl' as used herein is meant an alkyl group containing 1 to 4 carbon atoms and includes both straight and branched chains. A preferred lower alkyl group for R¹ is methyl.

Carboxy protecting groups used for R² include any protecting group known in the peptide art for protecting a carboxy function of an amino acid, for example alkyl esters of 1 to 6 carbon atoms, preferably the t-butyl ester. Methods for protecting and conditions for removing specific carboxy protecting groups are described in the literature—see for example Schroder & Lubke, *The Peptides*, Vol. 1 (Academic Press 1965).

The process of this invention employs a carbodiimide coupling agent or carbonyl diimidazole to effect reaction of the compounds of formulae II and III. Such coupling agents and methods for coupling using them are extensively described in the literature—see for example the aforementioned text book by Schroder & Lubke. Examples of carbodiimide coupling agents are dicyclohexylcarbodiimide (DCC), diisopropylcarbodiimide and 1-(3-dimethylamino)propyl-3-ethylcarbodiimide.

Preferably and for convenience the enantiomeric mixture of the acid of formula II is racemic.

The reaction is conveniently carried out using standard conditions for carbodiimide and carbonyl diimidazole couplings, e.g. using a solvent such as dichloromethane at about 0° C., and proceeds in high yield. Other solvents include CCl₄ and DMF.

Using the process of this invention it has been possible to prepare essentially quantitatively, a ca. 80:20 mixture of D, L and L, L diastereoisomers of formula I respectively using a racemic compound of formula II as starting material.

This result is contrary to the expectation that a racemic starting material would give equimolar quantities of diastereoisomers of formula I, should coupling be effected.

Compounds of formula I prepared by the process of this invention may be used to prepare captopril and analogous compounds, as described in U.S. Pat. No. 4,105,776 and 2,3-dihydro-1H-indole derivatives as described in South African Patent Application No. 80/4946 (E.P. Publication No. 24852), by reaction with an anion of a thioacid of formula (IV)

 (IV)

to give a compound of formula (V)

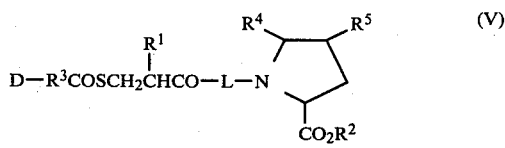 (V)

in excess of the corresponding L,L-diastereoisomer, in which formulae R¹, R², R⁴ and R⁵ are as defined above and R³ is lower alkyl, phenyl, or phenyl-lower alkyl. The product is then converted by ammonolysis and deprotection, in either order, into the desired final product (VI)

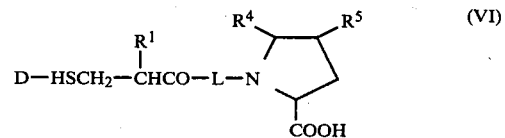 (VI)

wherein R¹ is lower alkyl, which can be separated from the corresponding L,L-isomer by fractional crystallisation or other conventional means.

Compounds of formula II used as starting materials for the process of this invention may be prepared by reacting a lower alkyl acrylic acid with hydrogen bromide. From this reaction preferred racemic starting materials are obtained.

Determination of the proportions of D,L and L,L diastereoisomers in the mixtures obtained in the process of this invention may be readily achieved by deprotecting to give the corresponding acids followed by observation of the relative intensities of the ¹Hnmr signals for the R¹ group, especially when R¹ is methyl. Of course a deprotection route should be chosen which does not alter the relative proportions.

Deprotection of the compounds of formula I when R² is tert-butyl can lead to such a change in proportions of isomers, vide infra. However, when R² is Buᵗ it is possible to observe the relative proportions of isomer directly by observation of the Buᵗ resonances in the ¹H nmr spectrum. High performance liquid chromatography may also be used.

The intermediates of formula I may also be employed in the preparation of captopril and analogous compounds via other routes using a deprotected acid intermediate. In particular the intermediates of formula I may be used to prepare captopril and analogous compounds as shown in the following reaction scheme:

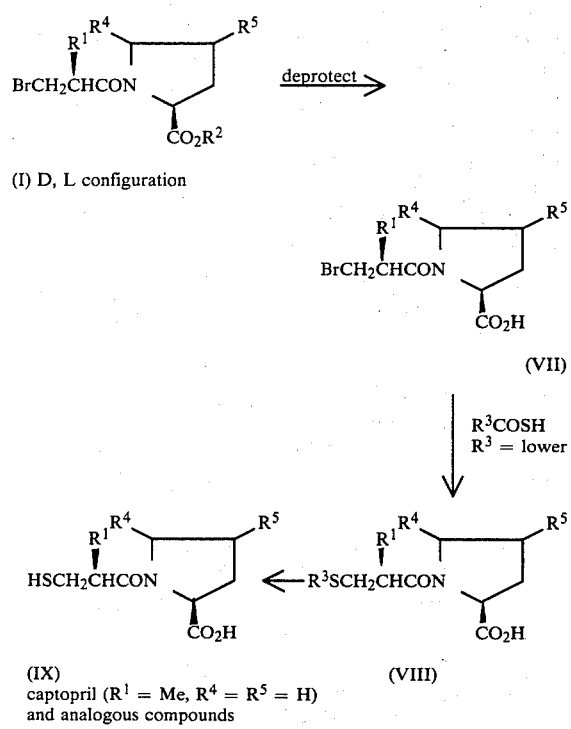

(I) D, L configuration (VII)

R³COSH
R³ = lower (IX) captopril (R¹ = Me, R⁴ = R⁵ = H) and analogous compounds (VIII)

It has surprisingly been found that when R² is tert-butyl, deprotection using trifluoroacetic acid (TFA) under standard conditions results in substantial racemisation of the propanoyl α-carbon, such that a 4:1 mixture of the compound of formula I and its L,L-diastereoisomer, can give a 3:2 mixture of the compound of formula VII and its L,L-diastereoisomer after a 1 hour reaction.

We have found that modification of the usual deprotection condition, but still using TFA, enables the excess of the preferred stereoisomer to be retained Accordingly a further aspect of this invention provides a process for preparing a compound of formula VII

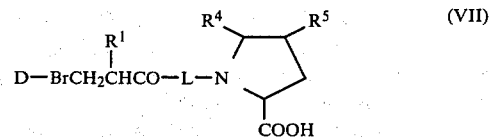

in excess of the corresponding L,L-diastereoisomer wherein R¹ is lower alkyl, which comprises reacting a compound of formula (X)

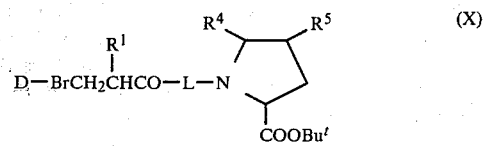

with trifluoroacetic acid at a low temperature (e.g. from about $-15°$ to $+20°$ C., preferably about $0°$ C., for a sufficiently short period of time to prevent substantial racemisation of the propanoyl α-carbon in the product of formula VII.

TFA deprotection to remove a t-butyl protecting group can involve reacting at room temperature for one hour or longer—see for example Biochemistry, Vol. 16, p5486 (1977). We have found that the stereochemistry of the starting materials is substantially retained when the TFA deprotection is carried out at a low temperature, e.g. $-5°$ to $15°$ C. and in a short period of time, for example, not more than 25 minutes, preferably not more than 20 minutes, most preferably not more than 15 minutes. In a typical TFA deprotection reaction complete retention of stereochemistry of starting materials was achieved by effecting reaction in about 10 minutes and at about $0°$ C., i.e. the proportion of D,L isomer of formula VII to L,L isomer was kept to about 80:20 (the same as in the starting materials of formula X). Reaction for longer periods was found to reduce the excess of the D,L-isomer. The table below shows how the proportion of D,L and L,L product varied as a function of time when 1-(D-3-bromo-2-methylpropionyl)-L-proline-t-butyl ester was deprotected using TFA at room temperature:

| Time (minutes) | % of isomers | |
| --- | --- | --- |
| | DL | LL |
| 2 | 78 | 22 |
| 10 | 78 | 22 |
| 20 | 67 | 33 |
| 30 | 63 | 37 |

Yet a further aspect of this invention relates to a stereospecific synthesis of 4S, 9aS cyclic L-proline derivatives having formula (XI)

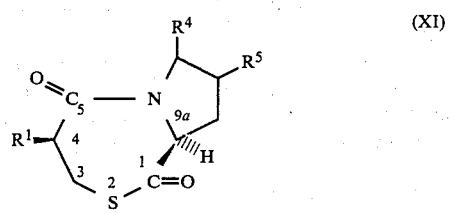

wherein R¹ is lower alkyl and R⁴ and R⁵ are as hereinbefore defined. Compounds of formula XI are useful as chemical intermediates and also as angiotensin converting enzyme inhibitors and potential antihypertensive agents. They are disclosed in U.S. Pat. No. 4,192,945 and South African Patent Application No. 80/4946 (E.P. Appln. No. 80,302,784.6, E.P. Publication No. 24852).

We have found a particularly convenient route to such stereoisomers employing stereoisomers of formula VII as hereinbefore defined. This route has the advantage of preparing the compounds of formula XI stereospecifically, thereby obviating the need to separate isomeric mixtures of final products. The isolation of the appropriate stereoisomer of formula VII, especially when prepared by the process hereinbefore described which provides increased proportions of the desired stereoisomer, is very easily effected. Also separation at an early stage avoids wasting reactant in preparing undesired isomers of the final product.

Accordingly this invention also provides a process for preparing a compound of formula (XI) as defined above which comprises (i) reacting a compound of formula VII as defined above, substantially free from the corresponding L,L-isomer, with an haloformate ester, e.g. an alkyl halo formate ester such as ethyl chloroformate, and a sulphide of formula (XII)

Y-SH     (XII)

wherein Y represents hydrogen or an alkali metal, e.g. sodium, with the proviso that when Y is hydrogen the heating is carried out in the presence of base, e.g. a tertiary amine, such as triethylamine, and (ii) cyclising the product of step (i) by heating, e.g. at 40° to 60° C., preferably about 45° C.

Conveniently the reaction step (ii) is carried out in the presence of a polar solvent, e.g. acetonitrile. This solvent may also be used for the first step of the reaction or other aprotic solvents such as methylene dichloride can be used. The method has the added advantage that a 'one-pot' process can be used to go from VII to XI.

It is understood that the above mentioned reaction process forms as an intermediate in situ a compound of formula (XIII)

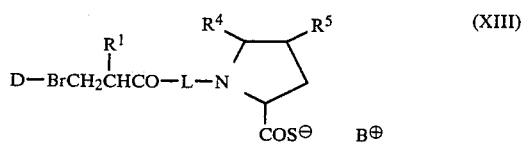

wherein $R^1$ is lower alkyl, $B^\oplus$ is a cation (derived from the base when Y is hydrogen), e.g. an alkali metal or an ammonium ion such as an alkylammonium cation. The compounds of formula XIII substantially free of L,L stereoisomers are also within the scope of this invention. Preferably $R^1$ is methyl. Preferably $B^\oplus$ is the triethylammonium ion.

This invention also provides a process for preparing a compound of formula XI as hereinbefore defined which comprises cyclising a compound of formula XIII by heating, preferably in the presence of a polar solvent such as acetonitrile. Preferably the cyclisation is effected at a temperature of from 40° to 60° C., e.g. about 45° C. The starting materials of formula VII may be prepared according to processes hereinbefore described. The desired D,L-stereoisomer may be separated from the corresponding L,L-stereoisomer (the former preferably already in excess) by converting the acid to its dicyclohexylamine (DCHA) salt and crystallising from an appropriate solvent, e.g. propan-2-ol whereby the desired D,L-form of the acid of formula VII is obtained as the DCHA salt. It may be converted to the acid by known means, e.g. treating with $KHSO_4$.

The compounds of formula VII and their dicyclohexylamine salts substantially free of L,L-stereoisomers are within the scope of this invention.

The following Examples further illustrate this invention:

EXAMPLE 1

1-(3-bromo-2-D-methylpropanoyl)-L-proline tert-butyl ester

Racemic 3-bromo-2-methylpropionic acid (50 g) in methylene dichloride (50 ml) was added over a ½ hour period to a solution of dicyclohexylcarbodiimide (60 g) in methylene chloride (400 ml) kept at −5° to 0° C. by external cooling. L-proline tert-butyl ester (50 g) in methylene dichloride (50 ml) was then added over a ½ hour period. The mixture was allowed to slowly warm to room temperature and left overnight. The precipitate formed in the reaction, was filtered and the filtrate evaporated. The residue was dissolved in diethyl ether (300 ml) and washed successively with 1 N HCl, water, 1 N NaOH and water. The ether layer was dried ($MgSO_4$) and evaporated to give a mixture (90 g) of the title compound in excess of 1-(3-bromo-2-L-methylpropanoyl)-L-proline, tert butyl ester.

Found: C, 48.5; H, 7.1; N, 4.35. $C_{13}H_{22}BrNO_3$ requires C, 48.8; H, 6.9; N, 4.4%

The relative isomer proportions were estimated to be 80:20 from the nmr spectrum of the tertiary butyl group in the product, in $CDCl_3$.

EXAMPLE 2

1-(3-Bromo-2-D-methylpropanoyl)-L-proline (a) To trifluoroacetic acid (300 g) cooled to 0° C. was added 1-(3-bromo-2-methylpropanoyl)-L-proline, t-butyl ester (90 g of an 80:20 mixture of D,L and L,L forms). The mixture was warmed to 25° C. and kept there for ¼ hour. The trifluoroacetic acid was removed by evaporation and azeotroping with carbon tetrachloride, and twice with toluene:propan-2-ol (30:70) and then diethyl ether. The relative isomer proportions were estimated from the same spectrum of the methyl group in the product, MeOH-$d_4$, NaOD solution. Signals appeared at δ 1.50 and 1.55 for D,L and L,L isomers respectively and were in the ratio 80:20.

(b) The residue was dissolved in diethyl ether (500 ml) and treated with excess di-cyclohexylamine (90 g). A solid formed and was filtered and recrystallised from propan-2-ol to give 1-(3-bromo-2-D-methylpropanoyl)-L-proline di-cyclohexylamine salt (83 g, 95% D,L form).

(c) The di-cyclohexylamine salt was converted back into the free acid by treatment with $KHSO_4$ solution (1 N 5 volumes) and it was extracted with methylene dichloride solvent. The solvent was removed by evaporation and the residue dissolved in $Na_2CO_3$ solution and this was washed with ether (3 x), acidified with HCl (2 N) and the acid was extracted with ether. After the ether solution had been dried ($MgSO_4$) and evaporated the residue was recrystallised from di-isopropyl ether to give 1-(3-bromo-2-D-methylpropanoyl)-L-proline as the monohydrate (m.p. 74°-5°).

Analysis: Found: C, 38.1; H, 5.7; N, 4.5, $C_9H_{14}BrNO_3$, $H_2O$ requires C, 38.3; H, 5.7; N, 5.0%.

EXAMPLE 3

(4S, 9aS)-Hexahydro-4-methyl-1H,5H-pyrrolo[2,1-c][1,4]thiazepine-1,5-dione. (cyclic captopril XI: $R^1$=Me, $R^4$=$R^5$=H)

A solution of 1-(3-bromo-2-D-methylpropanoyl)-L-proline (1.3 g) in $CH_2Cl_2$ (50 ml) was cooled to 0° C. and treated in turn with triethylamine (1 ml) then ethyl chloroformate (0.5 ml). After ¼ hour triethylamine (0.5 ml) was added and $H_2S$ gas was bubbled in at 20 ml/min for 20 minutes to give a mixture containing the triethylamine salt of 1-(3-bromo-2-D-methylpropanoyl)-L-Pro-SH. The solvent was removed by evaporation, then the residue dissolved in acetonitrile (50 ml) and heated at 45° C. for 4 hours. The solvent was removed by evaporation and the residue was dissolved in methylene dichloride. This solution was washed successively with water and $Na_2CO_3$ solution then dried and evaporated. The residue was extracted with diethyl ether and the solvent evaporated. The residue was extracted once more with diethyl ether and the solvent evaporated to give an oil (1 g) containing the title compound. The title compound was obtained on recrystallising from diethyl ether (0.2 g).

Analysis: Found: C, 54.7; H, 6.8; N, 6.85. $C_9H_{13}NO_2S$ requires C, 54.3; H, 6.6; N, 7.0%.

EXAMPLE 4

1-(3-Bromo-2-D-methylpropionyl)-L-proline t-butyl ester

To a solution of di-cyclohexylcarbodiimide (1.2 g) in dimethylformamide (DMF)(5 ml) at 0° C. was added racemic 3-bromo-2-methylpropionic acid (1 g) in DMF(5 ml) and then L-proline t-butyl ester (1 g) in DMF (5 ml). The mixture was stirred for 4 hours then poured on to $H_2O$ (30 ml), filtered and extracted with ether. The ether solution was washed with $H_2O$, N/10 HCl and $Na_2CO_3$ solutions, dried (MgSO_4) and evaporated. The residue (1.2 g) consisted of a 2:1 mixture of the title compound and its L,L isomer.

EXAMPLE 5

1-(3-Bromo-2-D-methylpropionyl)-L-proline-t-butyl ester

To a solution of di-cyclohexylcarbodiimide (3 g) in $CCl_4$ (20 ml) at 0° C. was added racemic 3-bromo-2-methylpropionic acid (2.5 g) in $CCl_4$ (5 ml) followed by L-proline t-butyl ester (2.5 g) in $CCl_4$ (5 ml). The mixture was stirred for 5 minutes, allowed to stand at ambient temperature for 18 hours and then filtered. The filtrate was washed with 2 N HCl, $H_2O$ and then $Na_2CO_3$ solution, dried (MgSO_4) and evaporated to give 3 g of a 4:1 mixture of the title compound and its L,L isomer.

EXAMPLE 6

1-(3-Bromo-2-D-methylpropionyl)-L-proline t-butyl ester

To a solution of 1,1-carbonyldiimidazole (2 g) in $CH_2Cl_2$ (20 ml) at 0° C. was added racemic 3-bromo-2-methylpropionic acid (2 g) in $CH_2Cl_2$ (5 ml) followed by L-proline t-butyl ester (2 g) in $CH_2Cl_2$ (5 ml). The mixture was stirred at 0° C. for 5 minutes, then allowed to stand at ambient temperature for 18 hours. It was then evaporated and the residue was dissolved in hexane and washed with dilute HCl, $H_2O$ and then $Na_2CO_3$ solution, dried (MgSO_4) and evaporated to give 2 g of a 4:1 mixture of the title compound and its L,L isomer.

EXAMPLE 7

1-(3-Bromo-2-D-methylpropionyl)-L-proline t-butyl ester

To a suspension of 1-(3-dimethylamino)propyl-3-ethylcarbodiimide hydrochloride (2.2 g) in $CH_2Cl_2$ (20 ml) at 0° C. was added racemic 3-bromo-2-methylpropionic acid (2 g) in $CH_2Cl_2$ (5 ml) followed by L-proline t-butyl ester (2 g) in $CH_2Cl_2$ (5 ml). The mixture was stirred at 0° C. for 5 minutes then allowed to stand at ambient temperature for 18 hours. The solvent was then removed by evaporation and the residue was dissolved in hexane and washed with dilute HCl, $H_2O$ and $N_2CO_3$ solution, dried (MgSO_4) and evaporated to give 3 g of a 4:1 mixture of the title compound and its L,L isomer.

I claim:

1. A process for preparing a compound of formula (I)

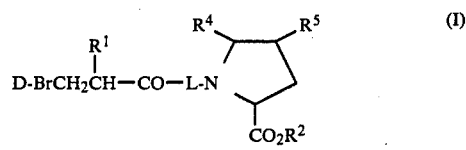

in excess of the corresponding L, L diastereoisomer in which the quantity of D,L-diasterioisomer exceeds the L,L-diasterioisomer at least by about 2:1 wherein $R^1$ is lower alkyl, $R^2$ is a carboxy protecting group, $R^4$ and $R^5$ either are both hydrogen or together with the carbon atoms to which they are attached represent a fused benzene ring optionally substituted by a group selected from hydroxy, lower alkyl, lower alkoxy and halogen, characterised in that a racemic mixture of an acid of formula (II)

is reacted with a carbodiimide or carbonyl diimidazole coupling agent and a compound of formula (III)

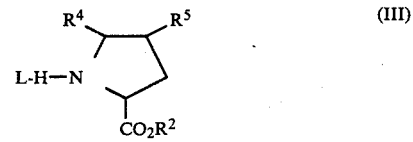

in which formulae $R^1$, $R^2$, $R^4$ and $R^5$ are as defined above.

2. A process as claimed in claim 1 wherein $R^2$ is an alkyl ester of 1 to 6 carbon atoms.

3. A process as claimed in claim 1 wherein the coupling agent is dicyclohexylcarbodiimide, diisopropylcarbodiimide, 1-(3-dimethylamino)propyl-3-ethylcarbodiimide or carbonyl diimidazole.

4. A process as claimed in claim 1 in which the quantity of D,L-diasterioisomer exceeds the L,L-diasterioisomer by about 4:1.

* * * * *